US00PP14435P39

(12) United States Plant Patent
Mukherjee et al.

(10) Patent No.: US PP14,435 P3
(45) Date of Patent: Dec. 30, 2003

(54) GLADIOLUS PLANT NAMED 'PALAMPUR PRINCESS'

(50) Latin Name: *Gladiolus hybrida*
Varietal Denomination: Palampur Princess

(75) Inventors: Devashish Mukherjee, Palampur (IN); Devendra Dhayani, Palampur (IN); Jaichand Rana, Simla (IN)

(73) Assignee: Council of Scientific and Industrial Research, New Delhi (IN)

( * ) Notice: Subject to any disclaimer, the term of this patent is extended or adjusted under 35 U.S.C. 154(b) by 43 days.

(21) Appl. No.: 10/205,398

(22) Filed: Jul. 26, 2002

(65) Prior Publication Data

US 2002/0199228 P1 Dec. 26, 2002

Related U.S. Application Data

(63) Continuation of application No. 09/813,829, filed on Mar. 22, 2001, now abandoned.

(51) Int. Cl.[7] ..... A01H 5/00

(52) U.S. Cl. ..... Plt./301

(58) Field of Search ..... Plt./301

*Primary Examiner*—Bruce R. Campell
*Assistant Examiner*—Annette Para
(74) *Attorney, Agent, or Firm*—Burns, Doane, Swecker & Mathis, L.L.P.

(57) ABSTRACT

A new variety of Gladiolus hybrida named 'Palampur Princess' is provided. Attractive flowers are formed in profusion in long spikes that are Dutch Vermillion with a center of Dresden Yellow in coloration. The growth habit is erect and substantially uniform. The leaves are dark green in coloration and contrast nicely with the bright flower coloration. The new variety is well suited for cut flower production and for growing as attractive ornamentation in the landscape.

1 Drawing Sheet

Figure 1:
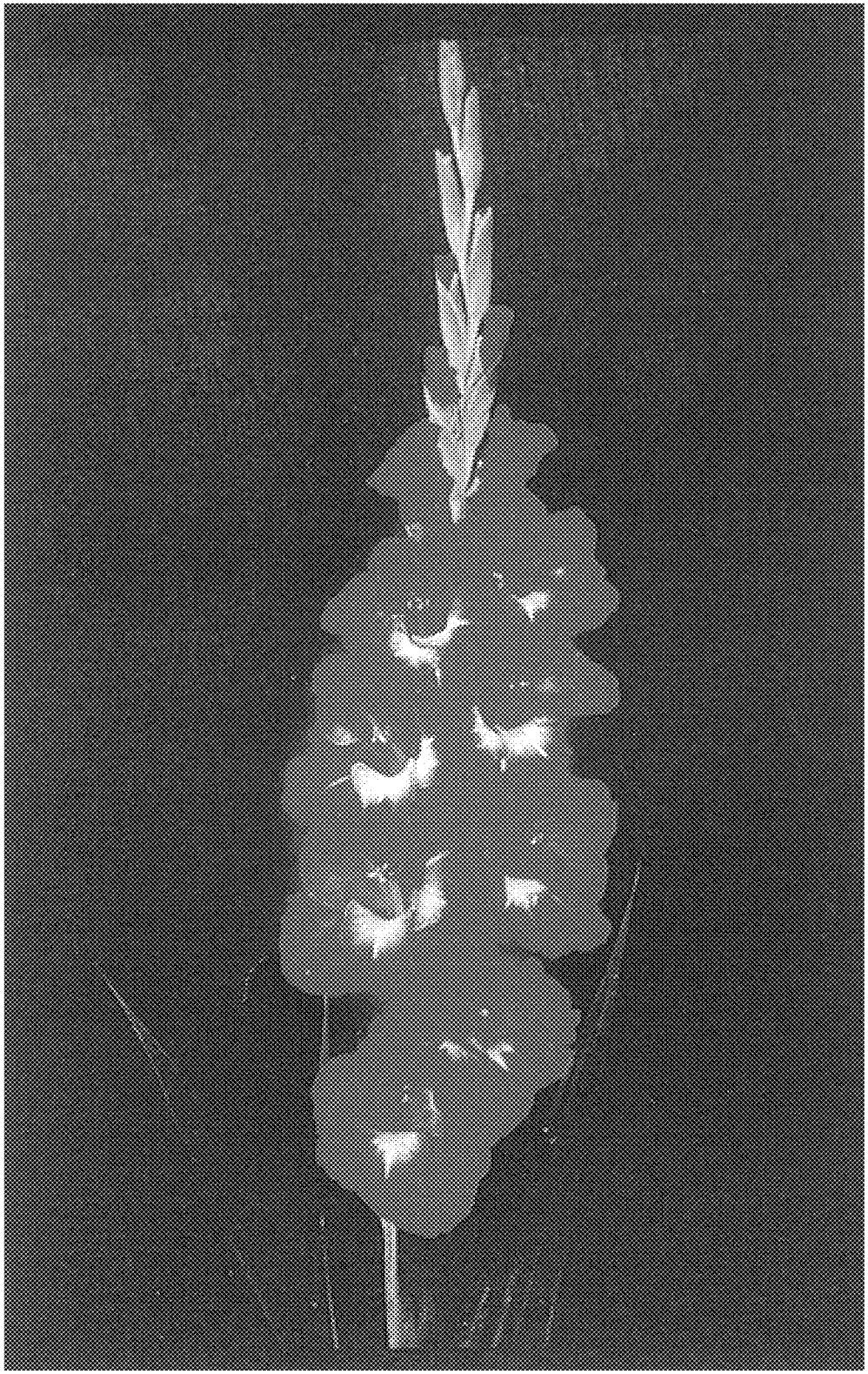

Botanical/commercial classification: Gladiolus hybrida/ Gladiolus or Sword Lily Plant.
Varietal denomination: cv. 'Palampur Princess'.

FIELD OF THE INVENTION

The present invention relates to a novel Gladiolus plant named 'Palampur Princess' and belongs to the Iridaceae family. The novel plant being a hybrid was developed in a planned breeding program. The novel 'Palampur Princess' plant is propagated vegetatively by the use of corms and hence readily can be maintained as a stable genotype. The plant of the invention is highly ornamental and can be widely cultivated for its beautiful flowers which are of commercial and export value.

BACKGROUND OF THE INVENTION

The present invention relates to a new and distinct variety of Gladiolus Plant, a member of the Gladiolus genus. The novel plant was formed by the cross of the 'Bonfire' variety (non-patented in the United States) and the 'Aldebaran' variety (non-patented in the United States). Each parent is botanically classified Gladiolus hybrida.

Gladiolus plants are important for cut flower production throughout the world. The commercial cultivation is widespread in temperate, tropical and subtropical climates. The demand of new varieties with better color, better quality flowers, and improved plant traits is always present in the floriculture trade.

In the modern garden Gladiolus cultivars come from diverse genetic parentages. They have cumulative heterozygosity for many characters inherent with the complex genetic constitution. In Gladiolus, diverse parents commonly are crossed together and the resulting cultivars and species that differ widely in chromosome numbers are also cross-fertile. In the present invention, the desirable strain obtained in the $F_1$ generation was perpetuated vegetatively without being segregated in the following generations unlike many cultivars which are available today that may be $F_2$, $F_3$ to $F_8$, etc. of a particular cross that are further blended with some additional parents at nearly every generation. Thus plants of the present invention are not allowed to segregate freely in further generations and are reproduced asexually. Because of this many available modern cultivars have become so complex that the offspring obtained by crossing them do not appear similar.

The planned breeding program that produced the new 'Palampur Princess' variety was carried out at the Institute of Himalayan Resources, Palampur Himachal Pradesh, India, with the goal to develop superior Gladiolus genotypes. Emasculation and pollination were conducted during the months of April and May, 1991. The resulting seeds were collected during July and August 1991 and were sown in field growing conditions during December 1991 and were covered with dry grass. The resultant seedlings were next space transplanted under field growing conditions during March and April 1992. Corms and cormels of these plants were replanted for the next four years and were continuously asexually multiplied and evaluated.

Based on the attractive color combination of the flowers, compactness of the flower spikes, number of flowers per spike, the length of flower spikes, the ruffled configuration of the flower petals, the number of flowers that remain open at a time, the number of corms and cormels produced per plant, and freedom from common diseases, a single plant of this invention was selected for further observation and evaluation. Initially, the plant was designated IHBT-GH-272 and subsequently was designated 'Palampur Princess'.

It was found that the new Gladiolus hybrida variety of the present invention exhibits the following combination of characteristics:

(a) exhibits an erect and substantially uniform growth habit, (b) forms in profusion on long spikes attractive flowers that are Dutch Vermillion with a center of Dresden Yellow in coloration;

(c) forms dark green leaves that contrast nicely with the bright flower coloration, and (d) is well suited for the production of cut flowers and for growing as attractive ornamentation in the landscape.

The new variety of the present invention can be readily distinguished from its parental varieties through an inspection of the flowers. The 'Palampur Princess' variety displays flowers that are Dutch Vermillion with a center of Dresden Yellow. This can be compared with red flowers of the 'Bonfire' variety and the yellow flowers of the 'Aldebaran' variety.

The new variety of the present invention has been asexually reproduced at Palampur, Himachal Pradesh, India through the division of corms and cormels beginning in 1992. Such asexual propagation has confirmed that the characteristics of the 'Palampur Princess' variety are firmly fixed and are reliably and stably transmitted to subsequent generations. No variants from the variety were observed.

DESCRIPTION OF THE PHOTOGRAPH

The accompanying photograph of FIG. 1 shows as reasonably possible to make the same in a color illustration of this character, a typical specimen of the mature flower spike and foliage of the 'Palampur Princess' variety. The plant had been asexually reproduced by division and was growing in the field during the summer at Palampur, Himachal Pradesh, India. The attractive Dutch Vermillion flowers having a Dresden Yellow center are shown.

DETAILED DESCRIPTION OF THE NEW VARIETY

The chart used in the identification of the colors is that of The Royal Horticultural Society (R.H.S. Colour Chart). The description is based upon the observation of mature plants that had been asexually reproduced by division and were growing in the field during the summer at Palampur, Himachal Pradesh, India. At this location the altitude is approximately 1300 m above sea level, the average maximum temperature is 30° C., the average minimum temperature is 10° C., and the average annual rainfall is approximately 250 cm.

Classification:

*Genus.*—Gladiolus.

*Species.*—Hybrida.

*Family.*—Iridaceae.

*Common name.*—Gladiolus/Sword Lily.

Plant:

*Plant height.*—Approximately 114 cm on average.

*Growth habit.*—Erect and substantially uniform.

*Stem diameter.*—Approximately 1.1 cm on average.

*Number of leaves/plant.*—Approximately 7.3 on average.

*Leaf shape.*—Lanceolate and sword-shaped, flattened and linear.

*Leaf disposition.*—Cauline and overlapped.

*Height of leaves.*—Commonly approximately 30.5 to 72.4 cm from ground level (approximately 57 cm on average).

*Width of leaves.*—Commonly approximately 3.1 to 4.9 cm (approximately 4 cm on average).

*Leaf apex.*—Acute or acuminate.

*Leaf base.*—Narrow.

*Leaf texture.*—Glabrous, scabrous due to strong and prominent substantially parallel venation that commonly is near white in coloration.

*Leaf margins.*—Entire.

*Leaf color.*—Green Group 137B on the upper surface and lighter green on the under surface.

*Corms/cormels.*—Commonly 1.8 corms per plant on average that commonly are approximately 5 cm in diameter. The number of cormels per plant commonly averages approximately 146.

Inflorescence:

*Days to flower.*—Commonly approximately 84.

*Type.*—Decorative, perianth petaloid, actinomorphic.

*Bud size.*—The lower three buds commonly are approximately 4.2 to 7.1 cm (average approximately 5.7 cm) in length, and approximately 0.86 to 1.49 (average approximately 1.1 cm) in width.

*Bud color.*—Red Group 44A.

*Number of spikes/plant.*—Approximately 1.8 on average.

*Length of the flower spike.*—Approximately 96 cm on average.

*Number of flowers/spike.*—Approximately 16 on average.

*Flower color.*—Dutch Vermillion, Red Group 40A, with center of Dresden Yellow, Yellow Group 5D.

*Petal number.*—Six tepals arranged in two whorls with three tepals on the inner whorl and three tepals on the outer whorl.

*Petal configuration.*—Polyphyllous, the tepals are stalked, oblong, oblanceolate, cuneate at the base, possess a blunt obtuse tip, and possess oblique lobes.

*Petal size.*—Commonly approximately 5.5 cm×approximately 7.5 cm.

*Petal margins.*—Entire and slightly ruffled.

*Number of flowers remaining open at one time.*—Approximately 8 on average.

*Longevity of the first flower.*—Approximately 3.2 days under normal growing conditions.

*Diameter of first flower.*—Approximately 9.8 cm on average.

*Longevity of the flower spike.*—Approximately 9.6 days on average.

*Style.*—Single, terminal, erect, approximately 5.5 to 6 cm in length, slightly curved, and soft white in coloration.

*Stigma.*—Trilobed, linear lobes, each lobe is approximately 5 mm in length, lobe apex is oblong, wavy, and purple-pink in coloration.

*Ovary.*—Inferior, and tricarpellary with many ovules in locule.

*Stamens.*—Three in number, triandrous, arranged in a whorl, adnate to tepals, filaments are approximately 3 to 3.5 cm in length, filaments are white in coloration, anthers are extrose, basifixed, light purple in coloration, and approximately 10 to 12 mm in length.

*Fragrance.*—None observed.

The 'Palampur Princess' variety has not been observed under all possible environmental conditions to date. Accordingly, it is possible that some variation in the phenotype may be observed when grown under different environmental conditions.

We claim:

1. A new and distinct Gladiolus hybrida plant having the following combination of characteristics:

(a) exhibits an erect and substantially uniform growth habit, (b) forms in profusion on long spikes attractive flowers that are Dutch Vermillion with a center of Dresden Yellow in coloration, (c) forms dark green leaves that contrast nicely with the bright flower coloration, and (d) is well suited for the production of cut flowers and for growing as attractive ornamentation in the landscape;

substantially as illustrated and described.

* * * * *